United States Patent
Pfeifer et al.

(10) Patent No.: US 6,912,914 B2
(45) Date of Patent: Jul. 5, 2005

(54) THREE DIMENSIONAL STRESS VECTOR SENSOR ARRAY AND METHOD THEREFOR

(75) Inventors: Kent Bryant Pfeifer, Los Lunas, NM (US); Thomas Jeffery Rudnick, St. Louis, MO (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 10/611,523

(22) Filed: Jul. 1, 2003

(65) Prior Publication Data

US 2005/0000298 A1 Jan. 6, 2005

(51) Int. Cl.$^7$ .............................................. G01N 3/08
(52) U.S. Cl. ...................................................... 73/818
(58) Field of Search ............................ 73/862.046, 172, 73/763, 862.68, 818, 780, 724; 600/484; 128/774; 324/725; 200/516

(56) References Cited

U.S. PATENT DOCUMENTS

| | | | | |
|---|---|---|---|---|
| 3,782,486 A | * | 1/1974 | Kuhn et al. | 177/210 R |
| 4,177,421 A | * | 12/1979 | Thornburg | 324/725 |
| 5,499,541 A | * | 3/1996 | Hopf et al. | 73/763 |
| 5,571,973 A | * | 11/1996 | Taylot | 73/862.046 |
| 5,597,984 A | * | 1/1997 | Mohaupt | 177/210 C |
| 5,678,448 A | * | 10/1997 | Fullen et al. | 73/172 |
| 5,760,530 A | * | 6/1998 | Kolesar | 310/339 |
| 5,775,332 A | * | 7/1998 | Goldman | 600/587 |
| 6,006,386 A | * | 12/1999 | Mohaupt | 73/862.68 |
| 6,216,545 B1 | * | 4/2001 | Taylor | 73/862.046 |

* cited by examiner

Primary Examiner—Max Noori
Assistant Examiner—Octavia Davis
(74) Attorney, Agent, or Firm—Richard B. O'Planick

(57) ABSTRACT

A sensor array is configured based upon capacitive sensor techniques to measure stresses at various positions in a sheet simultaneously and allow a stress map to be obtained in near real-time. The device consists of single capacitive elements applied in a one or two dimensional array to measure the distribution of stresses across a mat surface in real-time as a function of position for manufacturing and test applications. In-plane and normal stresses in rolling bodies such as tires may thus be monitored.

10 Claims, 2 Drawing Sheets

THREE DIMENSIONAL STRESS VECTOR SENSOR ARRAY AND METHOD THEREFOR

BACKGROUND OF THE INVENTION

The U.S. Government has certain rights in this invention as provided for by the terms of Contract No. DE-AC04-94AL85000 awarded by the U.S. Department of Energy. The Government has certain rights in the invention.

FIELD OF THE INVENTION

The invention relates generally to sensors for measuring stresses in near real-time in a myriad of manufacturing and test applications and, more specifically, to a sensor and method therefor for monitoring in-plane and normal stresses in rolling bodies such as tires.

Manufacture and processing of sheet materials often induce strain on materials due to non-uniform tensile stresses applied to the materials by pinch rollers in the process. This can lead to non-uniformities in the materials that later result in manufacturing problems. For example, woven goods do not have uniform ninety-degree angles between the warp and the pick threads across the sheet. This becomes a manufacturing problem further down the line when it becomes desirable to cut the material without cutting pick threads. An example of this problem is also found in the tire industry where polyester woven material is coated with rubber gum and used to make the bodies of tires. If, during the manufacture of the tire the pick threads are cut, a weakness will occur in the finished product.

Currently, this problem is avoided by cutting along the threads rather than perpendicular across the material, resulting in a sheet of material that is not perfectly square and requires mitigation. In addition, this process is slow compared to a single shearing operation. The total process could be greatly simplified by producing the woven sheet with a perpendicular pattern initially. This could be accomplished by using a sensor that would measure the in-plane and normal stresses on the material during manufacture and allow variations in the tension of the rollers to be adjusted to eliminate the non-uniform stresses. Achievement of means to accomplish such an adjustment may be made by replacing a single large roller with a set of several independent rollers whose tension is controlled by the sensor.

A further application in need of such a capability is in the manufacture of rolling bodies such as tires. Monitoring in-plane and normal stresses in tires during the manufacture thereof may also be utilized to eliminate non-uniform stresses. Tires for high-speed applications are subject to stresses whose characterization is important but currently is unavailable due to shortcomings in available technologies and analytical techniques. Tires at high speed undergo normal and shear stresses that are a result of aerodynamic loading effects and are a function of operating conditions such as wheel angular speed, slip angle, and temperature. Thus, there exists a need for technology development that can be used to measure both the magnitude and direction of the tire stresses on a test track with the car at high speed. Such technology needs to function on both straight road sections and on curves.

SUMMARY OF THE INVENTION

The subject invention satisfies the industry's need for a measuring the magnitude and direction of stresses in sheet materials, in general, and in rolling bodies such as tires specifically. According to one aspect of the invention, a sensor array, based upon capacitive techniques, is used to measure stresses at various positions in a sheet simultaneously and allows a stress map to be obtained in near real-time. The device comprises a mat with an array of capacitive sensors that measure the distribution of stresses across the mat's surface. Each individual sensor comprises a thin dielectric mat with a lower plane and an upper plane that is repositionable relative to the lower plane responsive to applied forces in an object body. Means for measuring the applied forces within the object body by measuring the movement of the upper mat plane responsive to such forces is provided. According to a further aspect of the invention, the mat is adapted to provide a plurality of lower electrodes disposed in a predetermined pattern and an upper electrode repositionable in at least one direction relative to the lower electrodes responsive to applied forces from the object body. The lower electrodes are capacitively coupled to an interrogation source, the capacitance between the lower electrodes and the interrogation source changing responsive to a change in position between the mat upper electrode and the mat lower electrodes. The sign and magnitude of the capacitance changes are compared and are indicative of the magnitude and direction of movement of the mat upper electrode relative to the mat lower electrodes that, in turn, is indicative of the stresses applied from the object body. Such movement further infers the three-dimensional magnitude and direction of stress forces within the object body. The sensors may be patterned into a linear array with each sensor isolated mechanically from the adjacent sensor to insure mechanical independence. By determining the displacement of the upper mat plane, the traction forces acting on the surface can be inferred.

According to a further aspect of the invention, a method for monitoring stresses in an object body is provided comprising the steps: locating a sensor in contact with the object body, the sensor comprising a mat having a lower plane and an upper plane repositionable relative to the lower plane in at least one direction responsive to the applied forces from the object body; and connecting means to the mat for measuring the applied forces from the object body by measuring the movement magnitude and direction of the upper mat plane relative to the lower mat plane. The sensors may further be arrayed into a mat configuration, each sensor consisting of a dielectric mat with electrodes to measure the position of an upper plate relative to bottom electrodes; the method further comprising the steps of mechanically isolating each sensor from an adjacent sensor; and determining the displacement of the plate to determine forces acting on an object body.

The subject invention satisfies the industry's need for a measuring the magnitude and direction of stresses in sheet materials, in general, and in rolling bodies such as tires specifically. According to one aspect of the invention, a sensor array, based upon capacitive techniques, is used to measure stresses at various positions in a sheet simultaneously and allows a stress map to be obtained in near real-time. The device comprises a mat with an array of capacitive sensors that measure the distribution of stresses across the mat's surface. Each individual sensor comprises a thin dielectric mat with a lower plane and an upper plane that is repositionable relative to the lower plane responsive to applied forces in an object body. Means for measuring the applied forces within the object body by measuring the movement of the upper mat plane responsive to such forces is provided. According to a further aspect of the invention, the mat is adapted to provide a plurality of lower electrodes disposed in a predetermined pattern and an upper electrode repositionable in at least one direction relative to the lower electrodes responsive to applied forces from the object body. The lower electrodes are capacitively coupled to an interrogation source, the capacitance between the lower electrodes and the interrogation source changing responsive to a change in position between the mat upper electrode and the mat lower electrodes. The sign and magnitude of the capacitance changes are compared and are indicative of the magnitude and direction of movement of the mat upper electrode relative to the mat lower electrodes that, in turn, is indicative of the stresses applied from the object body. Such movement further infers the three-dimensional magnitude and direction of stress forces within the object body. The sensors may be patterned into a linear array with each sensor isolated mechanically from the adjacent sensor to insure mechanical independence. By determining the displacement of the upper mat plane, the traction forces acting on the surface can be inferred.

According to a further aspect of the invention, a method for monitoring stresses in an object body is provided comprising the steps: locating a sensor in contact with the object body, the sensor comprising a mat having a lower plane and an upper plane repositionable relative to the lower plane in at least one direction responsive to the applied forces from the object body; and connecting means to the mat for measuring the applied forces from the object body by measuring the movement magnitude and direction of the upper mat plane relative to the lower mat plane. The sensors may further be arrayed into a mat configuration, each sensor consisting of a dielectric mat with electrodes to measure the position of an upper plate relative to bottom electrodes; the method further comprising the steps of mechanically isolating each sensor from an adjacent sensor; and determining the displacement of the plate to determine forces acting on an object body.

BRIEF DESCRIPTION OF THE DRAWINGS

The invention will be described by way of example and with reference to the accompanying drawings in which.

DETAILED DESCRIPTION OF THE PREFERRED EMBODIMENTS

Figure 1:
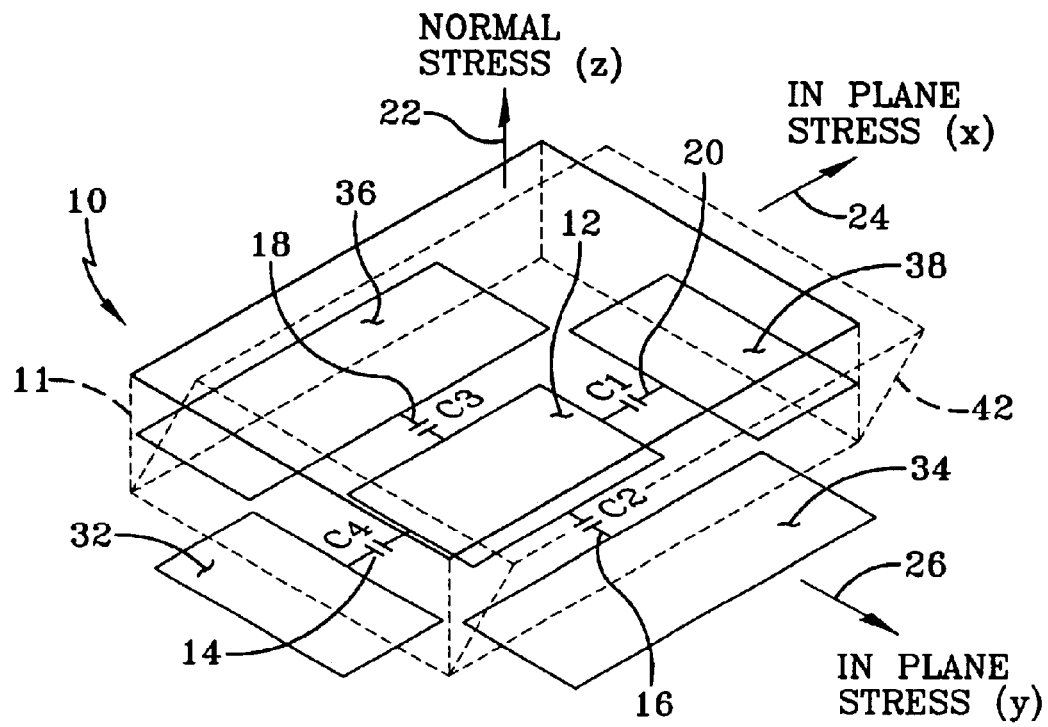
FIG. 1 is a schematic diagram of the subject capacitance stress sensor.
Figure 2:
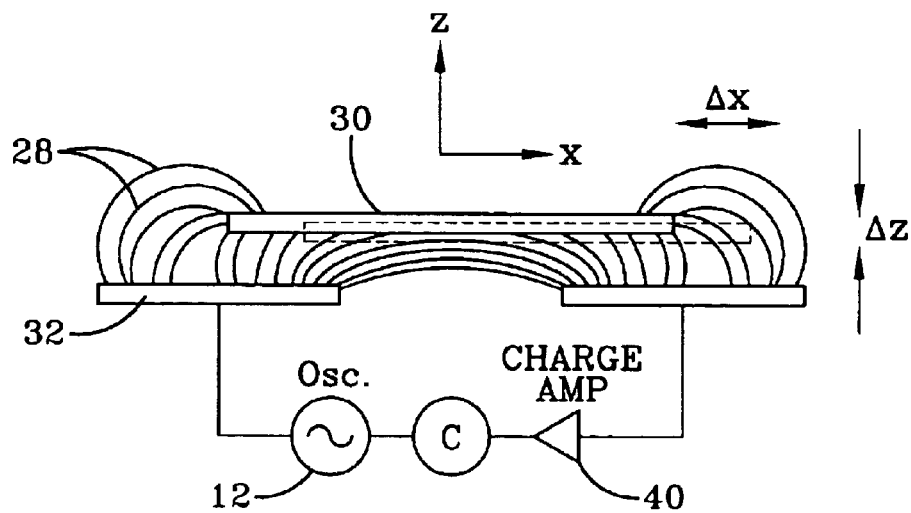
FIG. 2 is a side elevation view of the capacitance stress sensor showing electric field lines.

With initial reference to FIGS. 1 and 2, the subject invention generally provides a sensor 10 in the form of a mat 11 that measures the distribution of stresses across the mat's surface. FIG. 1 shows a schematic of the three-dimensional stress vector sensor 10 comprising, in the preferred embodiment an oscillator 12 (FIG. 2) and four capacitors formed between the plates 12 and plates 32, 34, 36, and 38 that are represented schematically by the capacitance symbols 14, 16, 18, and 20, respectively. For the purpose of the subject disclosure, normal stress is along the z-axis 22; in-plane stress along the x-axis 24; and in-plane stress along the y-axis 26. FIG. 2 demonstrates electric field lines 28 intercepted by a shunt plate 30 positioned at an upper plane of the mat 11 as shown. Four lower electrodes (also referred to herein as "capacitor plates") 32, 34, 36, and 38 are provided coupled to the oscillator plate 12 by their capacitance which is schematically illustrated by 14, 16, 18, and 20, respectively. The net capacitance is thus determined by the location of the shunt plane 30 above the capacitor plates 32, 34, 36, and 38. The oscillator 12 is shown connected in series with a charge amplifier 40. The oscillator, capacitors, and circuit components are commercially available in the industry. For the purposes herein, the oscillator 12 may be referred to as an "interrogation source" for intermittently ascertaining the stress forces imposed upon the mat by applied forces from an object body (not shown) in near real-time. However, other circuit configurations apparent to those skilled in the art may be employed that would facilitate an intermittent or continuous monitoring of the status of the capacitive elements in accordance with the invention if so desired. Hence, the term "interrogation source" is not intended in a limited definitional context but rather is intended to broadly refer to circuits coupled to the capacitive elements for the purpose of ascertaining the capacitive magnitude and direction of each.

An individual sensor 10, as described, consists of a thin dielectric mat 11 with bottom electrodes 32, 34, 36, and 38 and shunt plate 30 disposed in a spaced apart relationship. The choice of dielectric material is not critical and any such material conventional within the industry may be used. Moreover, as used herein, the term "mat" is used as a general reference to a sheet of material. No delimiting inference from the use of the term is intended as to the dimensions or configuration of the sheet or its surface configuration.

An array of sensors 10 is patterned into a linear (and ultimately 2-dimensional) array with each sensor 10 isolated mechanically from the adjacent sensor to insure mechanical independence. By precisely determining the displacement of the plate 30, one can infer the traction forces acting on the surface of an object body (not shown) against which the mat may be positioned.

From FIGS. 1 and 2, it will be noted that the fringe-field capacitance between the oscillator 12 and each of the capacitor plates 32, 34, 36, and 38 is a function of the location of the conductive plate 30 that rides above the mat. As the upper electrode 30 (surface) moves due to the applied forces, the capacitance between the center oscillator electrode 12 and each surrounding electrode 32, 34, 36, and 38 changes in magnitude. An exemplary change in the position of the top plate 30 relative to the lower electrodes is shown in FIG. in phantom at 42. The location of the shunt plate 30 determines what fraction of the electric field lines 28 is intercepted before reaching the opposite electrode and the resulting capacitance. Because the upper electrode 30 moves responsively to applied forces from an object body, the magnitude and direction of the applied forces may be ascertained by measurement of the change in capacitance between element 12, and elements 32,34,36, and 38.

Figure 3:
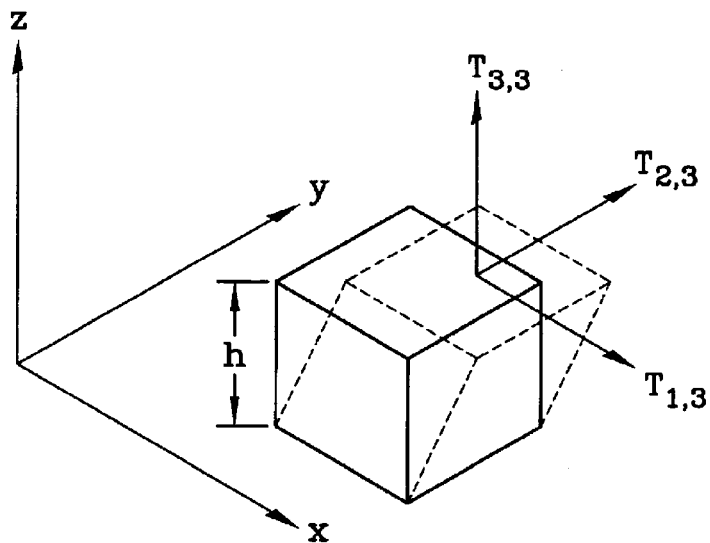
FIG. 3 is a diagram illustrating deformation of a volume of material under an arbitrary stress.

FIG. 3 shows a diagram of the deformation of a volume of material under an arbitrary stress $\vec{T} = T_{1,3}\hat{x} + T_{2,3}\hat{y} + T_{3,3}\hat{z}$. The compressibility is E', the shear modulus is $\mu$, and the height of the volume is h.

By comparing the sign and magnitude of the capacitance changes, the force (sign and magnitude) can be inferred. For example, if a stress were placed only normal to the sensor the grounding plate would move down causing a change in all four capacitors of the same magnitude and direction for each. Conversely, if a shear stress was placed on the sensor such that only movement in the x-direction occurred, then the capacitance between plates 12 and 36 (illustrated as $C_3$) and between plates 12 and 34 (illustrated as $C_2$) would remain the same, while the capacitance between plates 12 and 32 (illustrated as $C_4$) would decrease and the capacitance between plates 12 and 38 (illustrated as $C_1$) would increase. An ambiguous case is feasible wherein stress is applied in all three axis such as in the case of $\vec{T}=T_0(\hat{x}+\hat{y}+\hat{z})$; however, the design of the sensor allows complete separation of the stresses.

Considering the case where displacement of the plate is small compared to the thickness of the mat (see FIG. 3) to first order, the change in capacitance for each capacitor pair can be described as the following:

$$\Delta C_1 = A\Delta x - B\Delta z$$

$$\Delta C_2 = -A\Delta y - B\Delta z$$

$$\Delta C_3 = A\Delta y - B\Delta z$$

$$\Delta C_4 = -A\Delta x - B\Delta x \quad (1)$$

where A and B are experimentally determined constants, $\Delta C_n$ is the change in the $n^{th}$ capacitor and $\Delta x$, $\Delta y$, and $\Delta z$ are the displacements of the plate in each direction. The displacement of the top plate is related to the shear and normal stresses, and the mat's material constants, by the following relationships:

$$\Delta x = T_{13}\frac{h}{2\mu} \quad (2)$$

$$\Delta y = T_{23}\frac{h}{2\mu}$$

$$\Delta z = T_{33}\frac{h}{E'}$$

where h, $\mu$, and E' are the unstrained thickness, the shear modulus, and the compressibility of the mat, respectively, $T_{13}$ is the shear stress in the x-direction, $T_{23}$ is the shear stress in the y-direction, and $T_{33}$ is the normal stress. The stresses can be related to the capacitance by combining equations 1 and 2 as follows to calculate the stresses from the changes in capacitance:

$$T_{13} = \frac{\Delta C_4 - \Delta C_1}{A}\frac{\mu}{h} \quad (3)$$

$$T_{23} = \frac{\Delta C_3 - \Delta C_1}{A}\frac{\mu}{h}$$

$$T_{33} = \frac{\Delta C_4 - \Delta C_1}{2B}\frac{E'}{h}$$

In equation 3, it will be seen that the stresses are related to the changes in the capacitance only and are independent of the stresses in the other directions. Thus, the stresses can be uniquely resolved in three dimensions simultaneously via this measurement.

Heretofore, state of the art capacitive measurement techniques require very high input impedance operational amplifier systems that limit the selection of commercially available components to devices with bandwidths on the order of less than a few megahertz. Thus, the oscillator frequencies and the resulting measurement frequency are limited. An additional limitation is the physical size of the individual elements and the wiring necessary to monitor them. In the practice of the subject invention, a linear array of sensors can be constructed that consists of approximately 30–50 individual sensor elements (FIG. 1) on ¼" intervals and can be interrogated in a 14 $\mu$sec interval. A reliable 2-dimensional array would consist of 30 linear arrays arranged to give approximately 900 measurement elements over a 10" by 10" area with ¼" resolution. By redundancy of measurement hardware, larger arrays can be realized. It will be appreciated that the aforementioned dimensional and quantitative parameters specification is by way of example only. Other arrays having differing numbers of sensor elements spaced apart at different intervals may be devised and deployed if desired.

Figure 4:
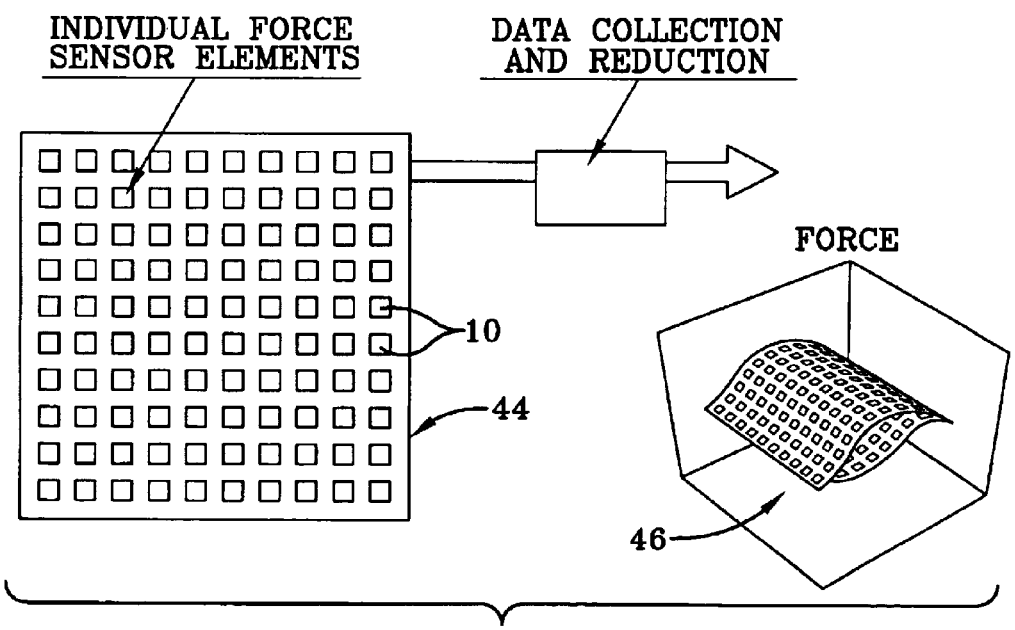
FIG. 4 is diagram of an array system configured pursuant to the invention and a map of force vectors as a function of location on the array.

A diagram of the array system 44 to convert data from an array of 3-D sensors to a map 46 of force vectors as a function of location on the array is shown in FIG. 4. Individual force sensor elements comprise the array and data is collected and reduced at block to yield the force map.

The arrays described above may be fabricated using conventional processing techniques to form thin planer arrays that may be adhesive backed and placed on both flat and curved surfaces. Consequently, the arrays will allow measurement of three dimensional stress at any point in a process.

Such devices will find application in any industry where non-uniform stresses need to be quantified in order to increase product yield. Currently, piezoelectric devices exist that measure magnitude of stress in one dimension. Thus, in order to measure data equivalent to the instant invention, an array would be required that incorporates three piezoelectric type elements for every one element of the capacitance sensor of the invention. In addition, the subject sensors of the present invention may be fabricated in very large arrays for a relatively small cost by utilizing conventional circuit board manufacturing processes. Finally, the subject sensor devices can be made very thin, less than 10 mils thick, if so desired. Such a thin profile allows far more application versatility than current technology.

Thus, from the foregoing, the subject invention provides an inexpensive, thin, stress sensor array that can be readily applied to many manufacturing operations without a major retrofit. Representative industries include, but are not limited to, tire manufacture, textile manufacture, or any other process that requires knowledge of stress magnitude and direction. For example, tires at high speed undergo normal and shear stresses that are a result of aerodynamic loading effects and are a function of operating conditions such as wheel angular speed, slip angle, and temperature. The subject array may be used, therefore, to measure both the magnitude and direction of the tire stresses on a test track with the car at high speed. The subject invention may function on both straight road sections and on curves.

Similarly, the subject array may be used to simultaneously measure stresses at various positions in a sheet, such as in textile fabrication, and allow a stress map to be obtained in near real-time. Such measurements and the data gathered therefrom may be useful in avoiding the introduction of strain on the materials due to non-uniform tensile stresses.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A sensor for measuring applied forces within an object body, comprising:

a mat having a lower plane comprising a plurality of discrete capacitor plates mutually arranged in a spaced apart two dimensional array about an interrogation electrode and an upper conductive plate repositionable relative to the plurality of discrete capacitor plates responsive to the applied forces from the object body; and means for measuring the applied forces within the object body by resolving and measuring in three dimensions a stress vector resulting from the movement of the upper mat conductive plate relative to the lower capacitor plates;

the mat comprises a dielectric body, and the plurality of discrete capacitor plates being capacitively coupled to the interrogation electrode and to the upper conductive plate and wherein the capacitance between the lower discrete capacitor plates and the interrogation electrode changes responsive to a change in position between the mat upper conductive plate and the mat lower capacitor plates; and the means for measuring the applied forces within the object body comprises means for comparing the sign and magnitude of the capacitance changes between the lower capacitor plates and the interrogation electrode.

2. A sensor for measuring applied forces within an object body, comprising:

a mat having a lower plane and an upper plane repositionable relative to the lower plane in at least one direction responsive to the applied forces from the object body; and means for measuring the applied forces within the object body by measuring the movement of the upper mat plane relative to the lower mat plane;

wherein the mat comprises a dielectric body having a plurality of lower electrodes disposed in a predetermined pattern and an upper electrode, the upper electrode being repositionable in at least one direction relative to the lower electrodes responsive to applied forces within the object body;

wherein each lower electrode is capacitively coupled to an interrogation source, the capacitance between the lower electrodes and the interrogation source changing responsive to a change in position between the mat upper electrode and the mat lower electrodes and wherein the means for measuring the applied forces within the object body comprises means for comparing the sign and magnitude of the capacitance changes between the lower electrodes and the interrogation source.

3. A sensor according to claim 2, wherein the lower electrodes are disposed in a predetermined pattern such that the capacitance changes between the lower electrodes and the interrogation source are indicative of the magnitude and direction of movement of the mat upper electrode relative to the mat lower electrodes.

4. A sensor according to claim 3, wherein the interrogation source is centrally disposed relative to the mat lower electrodes.

5. A sensor according to claim 3, wherein the lower electrodes are disposed in a predetermined pattern that resolves in three dimensions the applied forces within the object body.

6. A sensor according to claim 5, wherein the sign and magnitude of the applied forces is inferred exclusively from the sign and magnitude of changes in capacitance between the lower electrodes and the interrogation source.

7. A sensor for measuring applied force within an object body comprising:

a plurality of discrete sensor components attend into a linear array with each sensor component mechanically isolated from an adjacent sensor, each sensor component comprising a mat having a plurality of lower capacitor plates disposed about and capacitively coupled to an interrogation electrode and an upper conductive plate repositionable relative to the lower plane in at least one direction responsive to the applied forces within the object body; and means for measuring the applied force within th object body by measuring the movement of the upper mat conductive plate relative to the lower mat capacitor plates; and the means for measuring the applied force within the object body comprises means for comparing the sign and magnitude of capacitance changes between the lower capacitor plates and the interrogation electrode.

8. A method for measuring applied forces within an object body, comprising the steps:

(a) locating a sensor proximate the body, the sensor comprising a mat having a lower plane and an upper plane repositionable relative to the lower plane in at least one direction responsive to the applied forces within the object body;

(b) connecting means to the mat for measuring the applied forces within the object body by measuring the movement magnitude and direction of the upper mat plane relative to the lower mat plane; and wherein the mat is formed at least partially of dielectric material having a plurality of lower electrodes disposed in a predetermined pattern and an upper electrode repositionable in at least one direction relative to the lower electrodes responsive to applied forces, the method comprising the further steps:

capacitively coupling the lower electrodes to an interrogation source, the capacitance between the lower electrodes and the interrogation source changing responsive to a change in position between the mat upper electrode and the mat lower electrodes; and comparing the sign and magnitude of the capacitance changes between the lower electrodes and the interrogation source.

9. A method according to claim 8, wherein further comprising the step of placing a plurality of the sensors into a linear array with each sensor mechanically isolated from an adjacent sensor.

10. A method according to claim 9, wherein further comprising the step of placing a plurality of linear arrays of sensors into a two dimensional array with each sensor mechanically isolated from an adjacent sensor.

* * * * *